United States Patent
Biswas et al.

(10) Patent No.: US 11,540,990 B2
(45) Date of Patent: Jan. 3, 2023

(54) OIL COMPOSITION AND COSMETIC CONTAINING THE SAME

(71) Applicant: AJINOMOTO CO., INC., Tokyo (JP)

(72) Inventors: Shuvendu Biswas, Kawasaki (JP); Shiori Oono, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/832,276

(22) Filed: Mar. 27, 2020

(65) Prior Publication Data

US 2020/0306157 A1  Oct. 1, 2020

(30) Foreign Application Priority Data

Mar. 29, 2019 (JP) .............................. JP2019-065391

(51) Int. Cl.
| | | |
|---|---|---|
| A61K 8/42 | (2006.01) | |
| A61K 8/34 | (2006.01) | |
| A61K 8/02 | (2006.01) | |
| A61K 8/63 | (2006.01) | |
| A61Q 1/06 | (2006.01) | |

(52) U.S. Cl.
CPC .............. *A61K 8/42* (2013.01); *A61K 8/0229* (2013.01); *A61K 8/342* (2013.01); *A61K 8/63* (2013.01); *A61Q 1/06* (2013.01); *A61K 2800/10* (2013.01); *A61K 2800/43* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 5,153,340 A | 10/1992 | Ichikawa et al. | |
| 5,474,778 A | 12/1995 | Ichikawa et al. | |
| 2007/0009458 A1* | 1/2007 | Masuda | A61K 8/895 424/64 |
| 2014/0004065 A1* | 1/2014 | Souda | A61K 8/89 424/59 |
| 2014/0271510 A1 | 9/2014 | Takino et al. | |

FOREIGN PATENT DOCUMENTS

| | | |
|---|---|---|
| JP | 3-275697 | 12/1991 |
| JP | 5-286844 | 11/1993 |
| JP | 2002-161021 A | 6/2002 |
| JP | 2006-115110 A | 5/2008 |
| JP | 2009-73797 | 4/2009 |
| JP | 2009234991 | * 10/2009 |
| JP | 2010-030959 A | 2/2010 |
| JP | 2011-195554 A | 10/2011 |
| JP | 4854474 B2 | 11/2011 |
| JP | 2012-17297 | 1/2012 |
| JP | 2013-49633 | 3/2013 |
| JP | 2013-194035 A | 9/2013 |
| JP | 2014-024760 A | 2/2014 |
| JP | 2015-193607 A | 11/2015 |
| JP | 2017-014146 A | 1/2017 |
| JP | 2017-039669 A | 2/2017 |
| JP | 2017-071601 A | 4/2017 |
| WO | WO 2011/099422 A1 | 8/2011 |

OTHER PUBLICATIONS

Truth in Aging Phytostearyl/Beheny//Octyldodecy Lauroyl Glutamate Jun. 7, 2009.*
Dolce & Gabbana Perfect Reveal Lift Foundation . . . My Review + Swatches of Every Shade Oct. 24, 2014.*
French Preliminary Search Report and Written OPinion dated Oct. 16, 2020 in Patent Application No. FR 2003022 (with English translation of the Written Opinion and Category of cited Documents), 28 pages.
Office Action dated Sep. 5, 2022 regarding the corresponding Japanese Patent Application No. 2019-065391 (with English machine translation).

* cited by examiner

Primary Examiner — Danah Al-Awadi
(74) Attorney, Agent, or Firm — Oblon, McClelland, Maier & Neustadt, L.L.P.

(57) ABSTRACT

Oil compositions containing two or more mixtures selected from the group consisting of a lauroyl glutamic acid diester mixture having a melting point higher than 33° C., a lauroyl glutamic acid diester mixture having a melting point of 20 to 32° C., and a lauroyl glutamic acid diester mixture having a melting point of −20° C. or lower can simultaneously achieve the texture properties (melting smooth feel, uniform spread over the lip surface, and transparent gloss), stability (such as improvement in breaking strength and improvement in temporal stability of the breaking strength), and the elasticity necessary for improving makeup duration of a lipstick.

8 Claims, 1 Drawing Sheet

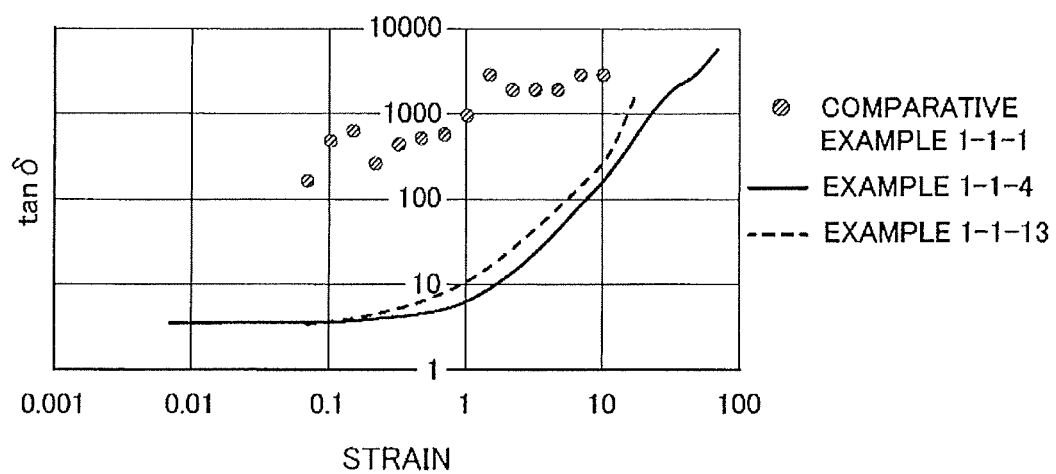

OIL COMPOSITION AND COSMETIC CONTAINING THE SAME

CROSS REFERENCES TO RELATED APPLICATIONS

This application claims priority to Japanese Patent Application No. 2019-065391, filed on Mar. 29, 2019, which is incorporated herein by reference in its entirety.

BACKGROUND OF THE INVENTION

Field of the Invention

The present invention relates to oil compositions, and more particularly to oil compositions capable of improving the texture properties and stability of a lipstick, and a cosmetic containing the same.

Discussion of the Background

When a lipstick is applied to the lip surface and the high-viscosity oil in the lipstick melts at or below the lip surface temperature (approximately 33° C.), the ingredients in the lipstick can spread uniformly on the lip surface and achieve uniform adhesion to make the lip surface look beautiful. Moreover, if an oil having a viscosity to some degree melts at or below the lip surface temperature, the lipstick applied to the lips can give a melting smooth feel (a feel felt by simultaneous action of close adhesion and slippery feel). However, if the melting point of the oil is too low, it is difficult to achieve such a melting feel. Moreover, if an oil having too low a melting point is blended in the lipstick, there is a problem that it is difficult to obtain a lipstick having a sufficiently high breaking strength, resulting in breakage of the lipstick when used.

For the purpose of increasing the breaking strength of the lipstick, it is generally known that a wax having a high melting point (a wax having a melting point of 50° C. or higher) is blended in the lipstick. However, there is a problem that blending a wax having a high melting point at a high concentration results in a heavy feel. Furthermore, since the wax has a melting point equal to or higher than the lip surface temperature, there is a problem such as poor transparency at or below the lip surface temperature, resulting in poor gloss of the lipstick after application to the lips.

Meanwhile, for the purpose of improving the hardness stability of a lipstick against the temperature, it is known that a combination of a high-viscosity oil having a relative permittivity of less than 2.5 (for example, hydrogenated polyisobutene) and a soft branched wax is effective (see Japanese Patent Application Publication No. 2012-17297, which is incorporated herein by reference in its entirety). However, it is known that the use of a high-viscosity oil such as polybutene reduces the makeup duration of the lipstick (see Japanese Patent Application Publication No. 2009-73797, which is incorporated herein by reference in its entirety). Moreover, there is a problem that a soft wax having low transparency such as microcrystalline wax leads to the suppression of gloss of the lipstick.

For the purpose of improving the makeup duration of the lipstick, it is known to blend both of a high-viscosity oil and a high-melting-point wax (having a melting point of 70° C. or higher) (see Japanese Patent Application Publication No. 2009-73797, which is incorporated herein by reference in its entirety). However, it is impossible to obtain a melting smooth feel while improving the breaking strength of the lipstick and its temporal stability.

In other words, it has been difficult to achieve a non-sticky, melting, and smooth feel and transparent gloss of the lipstick while improving the makeup duration and stability.

As oils which are excellent in improving the emulsifying property, the water holding property, the moisturizing capacity, the moisture permeability, and the barrier function of the stratum corneum, and which have little sticky feel when applied to the skin, ester compounds of N-lauroyl-L-glutamic acid and alcohol mixtures of phytosteryl alcohol (cyclic alcohol, P), 2-octyldodecyl alcohol (branched alcohol, OD), and behenyl alcohol (linear alcohol, B) have been developed (see Japanese Patent Application Publication No. Hei 3-275697, Japanese Patent Application Publication No. 2013-49633, and Japanese Patent Application Publication No. Hei 5-286844, which are incorporated herein by reference in their entireties). For example, an ester compound of N-lauroyl-L-glutamic acid and an alcohol mixture of phytosteryl alcohol, 2-octyldodecyl alcohol, and behenyl alcohol is developed and sold under the INCI (cosmetic ingredient name) of phytosteryl/behenyl/octyldodecyl lauroyl glutamate. These oils contain esters of phytosteryl alcohol (cyclic alcohol, P), 2-octyldodecyl alcohol (branched alcohol, OD), and behenyl alcohol (linear alcohol, B) in a certain molar ratio ((B+OD)/P=2.33) in the structure. However, these oils have a melting point of 35° C. or higher and do not melt at or below the lip surface temperature (approximately 33° C.). Therefore, when these oils are used for lipstick, there are problems such as difficulty in spreading uniformly on the lip surface, resulting in non-uniform adhesion. In addition, these oils have problems such as poor transparency at 33° C. and poor gloss of the lipstick when blended in the lipstick. Furthermore, there is also a problem that it is impossible to sufficiently improve the temporal stability of the breaking strength of the lipstick.

It is known, for example, to reduce the alcohol ratio (B/P) in preparation for the purpose of lowering the melting point of phytosteryl/behenyl/octyldodecyl lauroyl glutamate (see Japanese Patent Application Publication No. 2013-49633, which is incorporated herein by reference in its entirety). Phytosteryl/behenyl/octyldodecyl lauroyl glutamate having a melting point of 20° C. to 32° C. thus obtained is developed and sold. However, in the case where the oil, the melting point of which is lowered to 33° C. or lower by changing the feed ratio for production, is used for a lipstick, it is impossible to sufficiently improve the temporal stability of the breaking strength of the lipstick. Furthermore, the balance between the slipperiness and breaking strength of the lipstick blended with the oil thus obtained (=breaking strength of the lipstick/coefficient of dynamic friction of the lipstick) is not sufficiently high. As above, even when the feed ratio for production is changed to lower the melting point to 33° C. or lower, it is difficult to achieve both stability and feel.

In addition, an ester compound of N-lauroyl-L-glutamic acid and an alcohol mixture of phytosteryl alcohol (cyclic alcohol, P) and 2-octyldodecyl alcohol (branched alcohol, OD) is developed and sold under the INCI (cosmetic ingredient name) of phytosteryl/octyldodecyl lauroyl glutamate (see Japanese Patent Application Publication No. Hei 3-275697, Japanese Patent Application Publication No. 2013-49633, and Japanese Patent Application Publication No. Hei 5-286844, which are incorporated herein by reference in their entireties). However, these oils have a melting point of −20° C. or lower, and cannot sufficiently improve the breaking strength of the lipstick. In addition, these oils do not have sufficient elasticity, and cannot obtain sufficient makeup duration when used for a lipstick because the film of the lipstick ingredients on the lip surface is easily displaced by the movement of the lip.

SUMMARY OF THE INVENTION

Accordingly, it is one object of the present invention to provide novel oils which can simultaneously achieve the texture properties (melting smooth feel, uniform spread over the lip surface, and transparent gloss), stability (such as improvement in breaking strength and improvement in temporal stability of the breaking strength), and the elasticity necessary for improving makeup duration of a lipstick.

It is another object of the present invention to provide novel lipsticks which contain such an oil.

These and other objects, which will become apparent during the following detailed description, have been achieved by the inventors' discovery that it is possible to achieve the above objects by using an oil mixture in a lipstick, the oil mixture obtained by mixing at least two mixtures from a lauroyl glutamic acid diester mixture having a melting point higher than 33° C., lauroyl glutamic acid diester mixture having a melting point of 20 to 32° C., and a lauroyl glutamic acid diester mixture having a melting point of −20° C. or lower.

Thus, the present invention provides the following.

(1) An oil composition, comprising: two or more mixtures selected from the group consisting of a lauroyl glutamic acid diester mixture having a melting point higher than 33° C., a lauroyl glutamic acid diester mixture having a melting point of 20 to 32° C., and a lauroyl glutamic acid diester mixture having a melting point of −20° C. or lower.

(2) The oil composition according to (1), wherein one of the two or more lauroyl glutamic acid diester mixtures is contained in an amount higher than 10% by mass, and another one of the two or more lauroyl glutamic acid diester mixtures is contained in an amount higher than 10% by mass.

(3) The oil composition according to (1) or (2), wherein the lauroyl glutamic acid diester mixture having a melting point higher than 33° C. is obtained by reacting N-lauroyl-L-glutamic acid with an alcohol mixture containing two or more alcohols.

(4) The oil composition according to (3), wherein the alcohol mixture is an alcohol mixture of 2-octyldodecyl alcohol or isostearyl alcohol; phytosteryl alcohol; and behenyl alcohol.

(5) The oil composition according to any one of (1) to (4), wherein the lauroyl glutamic acid diester mixture having a melting point of 20 to 32° C. is obtained by reacting N-lauroyl-L-glutamic acid with an alcohol mixture containing two or more alcohols.

(6) The oil composition according to (5), wherein the alcohol mixture is an alcohol mixture of 2-octyldodecyl alcohol or isostearyl alcohol; phytosteryl alcohol; and behenyl alcohol.

(7) The oil composition according to any one of (1) to (6), wherein the lauroyl glutamic acid diester mixture having a melting point of −20° C. or lower is obtained by reacting N-lauroyl-L-glutamic acid with an alcohol mixture containing two or more alcohols.

(8) The oil composition according to (7), wherein the alcohol mixture is an alcohol mixture of 2-octyldodecyl alcohol or isostearyl alcohol and phytosteryl alcohol.

(9) The oil composition according to any one of (1) to (8), wherein a complex viscosity at 33° C. is 1 to 25000 Pa·s.

(10) A cosmetic, comprising: the oil composition according to any one of (1) to (9); and further at least one of a pigment and a colorant.

(11) The cosmetic according to (10), which is usable on a lip surface.

(12) A stick-form cosmetic, comprising: the oil composition according to any one of (1) to (9); and further an oil gelling agent having a melting point of 40° C. or higher.

(13) The stick-form cosmetic according to (12), further comprising at least one of a pigment and a colorant.

(14) The stick-form cosmetic according to (12) or (13), which is usable on a lip surface.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 illustrates a viscoelastic profile of an oil mixture.

DETAILED DESCRIPTION OF THE PREFERRED EMBODIMENTS

The oil composition of the present invention comprises two or more mixtures selected from the group consisting of a lauroyl glutamic acid diester mixture having a melting point higher than 33° C., a lauroyl glutamic acid diester mixture having a melting point of 20 to 32° C., and a lauroyl glutamic acid diester mixture having a melting point of −20° C. or lower. The oil composition of the present invention has a melting point of preferably 33° C. or lower, more preferably −15 to 33° C., and further preferably −5 to 31° C. In addition, the oil composition of the present invention preferably contains one of the two or more lauroyl glutamic acid diester mixtures in an amount higher than 10% by mass, and another one of the two or more lauroyl glutamic acid diester mixtures in an amount higher than 10% by mass. The oil composition of the present invention more preferably contains one of the two or more lauroyl glutamic acid diester mixtures in an amount of at least 20% by mass, and another one of the two or more lauroyl glutamic acid diester mixtures in an amount of at least 20% by mass. For example, in the oil composition of the present invention, the lauroyl glutamic acid diester mixture having a melting point higher than 33° C. is contained in an amount higher than 10% by mass and less than 90% by mass, and the lauroyl glutamic acid diester mixture having a melting point of 20 to 32° C. is contained in an amount higher than 10% by mass and less than 90% by mass. Preferably, in the oil composition, the lauroyl glutamic acid diester mixture having a melting point higher than 33° C. is contained in an amount of 20% by mass to 80% by mass, and the lauroyl glutamic acid diester mixture having a melting point of 20 to 32° C. is contained in an amount of 20% by mass to 80% by mass. More preferably, in the oil composition, the lauroyl glutamic acid diester mixture having a melting point higher than 33° C. is contained in an amount of 20% by mass to 40% by mass, and the lauroyl glutamic acid diester mixture having a melting point of 20 to 32° C. is contained in an amount of 60% by mass to 80% by mass. In addition, for example, in the oil composition of the present invention, the lauroyl glutamic acid diester mixture having a melting point higher than 33° C. is contained in an amount higher than 10% by mass and less than 90% by mass, and the lauroyl glutamic acid diester mixture having a melting point of −20° C. or lower is contained in an amount higher than 10% by mass and less than 90% by mass. Preferably, in the oil composition, the lauroyl glutamic acid diester mixture having a melting point higher than 33° C. is contained in an amount of 20% by mass to 80% by mass, and the lauroyl glutamic acid diester mixture having a melting point of −20° C. or lower is contained in an amount of 20% by mass to 80% by mass. More preferably, in the oil composition, the lauroyl glutamic acid diester mixture having a melting point higher than 33° C. is contained in an amount of 20% by mass to 40% by mass, and the lauroyl glutamic acid diester mixture having a melting point of −20° C. or lower is contained in an amount of 60% by mass to 80% by mass. In addition, for example, in the oil composition of the present invention, the lauroyl glutamic acid diester mixture having a melting point of 20 to 32° C. is contained in an amount higher than 10% by mass and less than 90% by mass, and the lauroyl glutamic acid diester mixture having a melting point of −20° C. or lower is contained in an amount higher than 10% by mass and less than 90% by mass. Preferably, in the oil composition, the lauroyl glutamic acid diester mixture having a melting point of 20 to 32° C. is contained in an amount of 20% by mass to 80% by mass, and the lauroyl glutamic acid diester mixture having a melting point of −20° C. or lower is contained in an amount of 20% by mass to 80% by mass.

The lauroyl glutamic acid diester mixture having a melting point higher than 33° C. can be obtained by, for example, reacting N-lauroyl-L-glutamic acid with an alcohol mixture containing two or more alcohols. For example, Japanese Patent Application Publication No. Hei 3-275697, Japanese Patent Application Publication No. 2013-49633, Japanese Patent Application Publication No. Hei 5-286844, which are incorporated herein by reference in their entireties, and the like describe a method of preparing an N-long-chain acyl acidic amino acid diester mixture, and with reference to these literature, the lauroyl glutamic acid diester mixture can be easily prepared. In addition, the ratios of the alcohols can be determined by, for example, stirring and heating the obtained lauroyl glutamic acid ester mixture in potassium hydroxide/ethanol TS for 1 hour to completely hydrolyze the ester mixture, and examining the content of the alcohols. Moreover, the melting point of the lauroyl glutamic acid ester mixture can be easily adjusted by measuring the melting point of the obtained lauroyl glutamic acid ester mixture, examining the relationship with the content of the alcohols, and adjusting the content of the alcohols. In addition, Japanese Patent Application Publication No. 2013-49633, which is incorporated herein by reference in its entirety, discloses the content and melting points of the alcohols, and reference to these also makes it possible to easily adjust the melting point of the lauroyl glutamic acid ester mixture. Examples of the alcohols contained in the alcohol mixture to be reacted with N-lauroyl-L-glutamic acid include sterols, aliphatic alcohols having 8 to 30 carbon atoms and being in the liquid form at room temperature, and solid higher alcohols having 12 to 38 carbon atoms. Examples of the sterols include phytosteryl alcohol, cholesterol, lanosterol, stigmasterol, and hydrogenated products thereof. Examples of the aliphatic alcohols include branched alcohols such as 2-octyldodecyl alcohol, isostearyl alcohol, and hexyldecyl alcohol, and unsaturated alcohols such as oleyl alcohol. Examples of the higher alcohols include cetyl alcohol and behenyl alcohol. The alcohol mixture to be reacted with N-lauroyl-L-glutamic acid is preferably an alcohol mixture of 2-octyldodecyl alcohol or isostearyl alcohol, phytosteryl alcohol, and behenyl alcohol.

Specific examples of the lauroyl glutamic acid diester mixture having a melting point higher than 33° C. include cholesteryl/behenyl/octyldodecyl lauroyl glutamate, phytosteryl/behenyl/octyldodecyl lauroyl glutamate, and isostearyl/phytosteryl/behenyl lauroyl glutamate, and preferable examples thereof include phytosteryl/behenyl/octyldodecyl lauroyl glutamate and isostearyl/phytosteryl/behenyl lauroyl glutamate.

The lauroyl glutamic acid diester mixture having a melting point of 20 to 32° C. can be obtained by, for example, reacting N-lauroyl-L-glutamic acid with an alcohol mixture containing two or more alcohols. As described above, reference to conventional techniques makes it possible to easily prepare a lauroyl glutamic acid diester mixture, and to easily adjust the melting point of a lauroyl glutamic acid ester mixture. The alcohols contained in the alcohol mixture to be reacted with N-lauroyl-L-glutamic acid are the same as those used for preparing a lauroyl glutamic acid diester mixture having a melting point higher than 33° C. The alcohol mixture to be reacted with N-lauroyl-L-glutamic acid is preferably an alcohol mixture of 2-octyldodecyl alcohol or isostearyl alcohol, phytosteryl alcohol, and behenyl alcohol.

Specific examples of the lauroyl glutamic acid diester mixture having a melting point of 20 to 32° C. include cholesteryl/behenyl/octyldodecyl lauroyl glutamate, phytosteryl/behenyl/octyldodecyl lauroyl glutamate, and isostearyl/phytosteryl/behenyl lauroyl glutamate, and preferable examples thereof include phytosteryl/behenyl/octyldodecyl lauroyl glutamate and isostearyl/phytosteryl/behenyl lauroyl glutamate.

The lauroyl glutamic acid diester mixture having a melting point of −20° C. or lower can be obtained by, for example, reacting N-lauroyl-L-glutamic acid with an alcohol mixture containing two or more alcohols. As described above, reference to conventional techniques makes it possible to easily prepare a lauroyl glutamic acid diester mixture, and to easily adjust the melting point of a lauroyl glutamic acid ester mixture. The alcohols contained in the alcohol mixture to be reacted with N-lauroyl-L-glutamic acid are the same as those used for preparing a lauroyl glutamic acid diester mixture having a melting point higher than 33° C. The alcohol mixture to be reacted with N-lauroyl-L-glutamic acid is preferably an alcohol mixture of 2-octyldodecyl alcohol or isostearyl alcohol and phytosteryl alcohol.

Specific examples of the lauroyl glutamic acid diester mixture having a melting point of −20° C. or lower include cholesteryl/octyldodecyl lauroyl glutamate, dihexyldecyl lauroyl glutamate, diisostearyl lauroyl glutamate, dioctyldodecyl lauroyl glutamate, octyldodecyl/phytosteryl lauroyl glutamate, and isostearyl/phytosteryl lauroyl glutamate, and preferable examples thereof include octyldodecyl/phytosteryl lauroyl glutamate.

The oil composition of the present invention has an appropriate viscoelasticity and is effective for the makeup duration of a lipstick. As for the oil composition of the present invention, the complex viscosity at 33° C. is preferably 1 to 25000 Pa·s, more preferably 3 to 1500 Pa·s, and further preferably 5 to 800 Pa's.

The cosmetic of the present invention contains the above-described oil composition and at least one of a pigment and a colorant. The cosmetic of the present invention can be used for the purpose of adjusting the skin color, hiding skin defects, and improving the skin condition, for the purpose of shielding ultraviolet rays, or for the purpose of coloring the face and lips to make them beautiful, and can be in various forms such as liquid, emulsion, ointment, cream, powder, and solid. The cosmetic of the present invention is preferably a cosmetic which is usable on the lip surface. In the cosmetic of the present invention, the above-described oil composition is contained in an amount of preferably 0.1 to 80% by mass, more preferably 0.5 to 40% by mass, and further preferably 1 to 20% by mass. Examples of the pigment and colorant include white pigments, colored pigments, extender pigments, and pearl pigments. Examples of the white pigments include titanium oxide and zinc oxide. Examples of the colored pigments include inorganic red pigments such as iron oxide, iron hydroxide, and iron titanate, inorganic brown pigments such as γ-iron oxide, inorganic yellow pigments such as yellow iron oxide and loess, inorganic black pigments such as black iron oxide and carbon black, inorganic purple pigments such as manganese violet and cobalt violet, inorganic green pigments such as chromium hydroxide, chromium oxide, cobalt oxide, and cobalt titanate, inorganic blue pigments such as navy blue and ultramarine blue, tar colorants (pigments) (such as Red No. 202, Red No. 204, Red No. 205, Red No. 220, Red No. 228, Yellow No. 401, Blue No. 404, Orange No. 203, and Orange No. 204), lakes of red tar colorants (dyes) (such as Red No. 3, Red No. 104, Red No. 106, Red No. 201, Red No. 226, Red No. 227, Red No. 230, Red No. 401, Red No. 505, Yellow No. 4, Yellow No. 5, Yellow No. 202, Yellow No. 203, Yellow No. 204, Blue No. 1, Blue No. 2, Blue No. 201, Green No. 3, Green No. 201, Green No. 204, Green No. 205, Orange No. 201, Orange No. 206, and Orange No. 207), lakes of natural colorants (such as carminic acid, laccaic acid, carthamin, brazilin, and crocin), and synthetic resin powders obtained by compounding these powders. Examples of the extender pigments include silicic acids such as silica and hydrated silica; silicates such as aluminum silicate and magnesium silicate; clay minerals such as talc, kaolin, bentonite, mica, and sericite; phosphate minerals such as hydroxyapatite; metal oxides such as aluminum oxide and magnesium oxide; alkaline earth metal carbonates such as light calcium carbonate, heavy calcium carbonate, light magnesium carbonate, and heavy magnesium carbonate; alkaline earth metal sulfates such as magnesium sulfate, barium sulfate (including plate form barium sulfate, butterfly form barium sulfate, and the like); boron nitride; organic powders such as lauroyl lysine and metal soaps; plate form synthetic powders such as synthetic mica; resin powders such as nylon beads, nylon powder, and silicone beads. Moreover, these powders may be subjected to surface treatment such as silicone treatment, fluorine compound treatment, silane coupling agent treatment, silane treatment, organic titanate treatment, acylated lysine treatment, fatty acid treatment, metal soap treatment, oil treatment, and amino acid treatment. Examples of the pearl pigments include titanium oxide-coated mica, bismuth oxychloride, titanium oxide-coated bismuth oxychloride, titanium oxide-coated talc, fish scale foil, and titanium oxide-coated colored mica. In the cosmetic of the present invention, the pigment and colorant are contained in an amount of preferably 0.1 to 50% by mass, more preferably 1 to 20% by mass, and further preferably 2 to 10% by mass.

The stick-form cosmetic of the present invention contains the above-described oil composition and an oil gelling agent having a melting point of 40° C. or higher. Examples of the oil gelling agent include waxes which can solidify oil opaquely, materials which can solidify oil transparently, and materials which thicken oil. Examples of the waxes include animal waxes, vegetable waxes, mineral waxes, and synthetic waxes.

Examples of the vegetable waxes include rice bran wax, caranuba wax, and candelilla wax, examples of the animal waxes include beeswax and gay wax, and examples of the mineral waxes and synthetic waxes include ceresin, solid paraffin, microcrystalline wax, polyethylene wax, and polyolefin wax. Exemplified among the mineral waxes and synthetic waxes are polyethylene wax, linear synthetic hydrocarbon wax having a molecular weight of 300 to 1000, and the like each having a melting point of 100° C. or higher, polyethylene wax, ceresin wax, linear synthetic hydrocarbon wax having a molecular weight of 300 to 1000, and the like each having a melting point lower than 100° C. and 90° C. or higher, polyethylene wax, polypropylene wax, ceresin wax, linear synthetic hydrocarbon wax having a molecular weight of 300 to 1000, paraffin wax, and the like each having a melting point lower than 90° C. and 80° C. or higher, polyethylene wax, ceresin wax, linear synthetic hydrocarbon wax having a molecular weight of 300 to 1000, paraffin wax, and the like each having a melting point lower than 80° C. and 70° C. or higher, ceresin wax, linear synthetic hydrocarbon wax having a molecular weight of 300 to 1000, paraffin wax, microcrystalline wax, and the like each having a melting point lower than 70° C. and 60° C. or higher, and ceresin wax, linear synthetic hydrocarbon wax having a molecular weight of 300 to 1000, paraffin wax, microcrystalline wax, and the like each having a melting point lower than 60° C. Particularly preferable are ceresin wax having a melting point of 70° C. or higher and lower than 77° C., purified paraffin wax having a melting point of 65° C. or lower, microcrystalline wax having a melting point of 60° C., polyethylene wax having a melting point of 85° C. or higher, and linear synthetic hydrocarbon wax having a melting point of 77° C. or higher and lower than 85° C. and a molecular weight of 300 to 1000.

Examples of the material which can solidify oil transparently include a gelling agent composed of a dextrin derivative, a low molecular gelling agent having multiple amide bonds, and a gelling agent composed of a high polymer or a derivative thereof. Examples of the gelling agent composed of a dextrin derivative include dextrin palmitate/hexyldecanoate, dextrin palmitate, dextrin palmitate/ethylhexanoate, dextrin myristate, and inulin stearate. Examples of the low molecular weight gelling agent having multiple amide bonds include dibutyl lauroyl glutamide and N-2-ethylhexanoyl-L-glutamic acid dibutylamide, and examples of the gelling agent composed of a high polymer or a derivative thereof include polyamide-3, polyamide-8, and polyamide-5.

The stick-form cosmetic of the present invention may further contain at least one of a pigment and a colorant. The pigment and colorant used in the stick-formed cosmetic of the present invention are the same as those used in the above-described cosmetic. The stick-form cosmetic of the present invention is preferably a stick-form cosmetic which is usable on the lip surface.

In the stick-form cosmetic of the present invention, the oil gelling agent having a melting point of 40° C. or higher is contained in an amount of preferably 0.2 to 50% by mass, more preferably 2 to 20% by mass, and further preferably 5 to 15% by mass. In the stick-form cosmetic of the present invention, the above-described oil composition is contained in an amount of preferably 0.1 to 50% by mass, more preferably 0.5 to 40% by mass, and further preferably 2 to 20% by mass. In the stick-form cosmetic of the present invention, the pigment and colorant are contained in an amount of preferably 0.1 to 30% by mass, more preferably 0.5 to 20% by mass, and further preferably 2 to 10% by mass.

In the cosmetic or stick-form cosmetic of the present invention, additional liquid oils, semi-solid oils, and the like usually used for cosmetics and pharmaceuticals can be used without any particular limitation as long as the effects of the present invention are not impaired.

Examples of the liquid oils include higher alcohols such as octyldodecanol, hexyldecanol, isostearyl alcohol, and stearyl alcohol; higher fatty acids such as isostearic acid; linear or branched hydrocarbon oils such as liquid paraffin, hydrogenated (hydrogen-added) polyisobutene, squalane, and squalene; vegetable oils such as shea butter, almond oil, jojoba oil, olive oil, jojoba seed oil, corn germ oil, wheat germ oil, meadowfoam oil, sunflower oil, and macadamia nut oil; animal oils and/or fats such as liquid lanolin; ester oils of fatty acid esters and polyhydric alcohol fatty acid esters such as bis-diglyceryl polyacyladipate-2, diisostearyl malate, isopropyl myristate, cetyl ethylhexanoate, cetyl palmitate, isopropyl palmitate, caprylic/capric triglyceride, triisostearin, and triethylhexanoin; acyl amino acid esters such as isopropyl lauroyl sarcosinate (ELDEW (registered trademark) SL-205), hexyldecyl myristoyl methylaminopropionate, bis(hexyldecyl/octyldodecyl) lauroyl glutamate, and dioctyldodecyl stearoyl glutamate; silicone oils such as cyclopentasiloxane, dimethylpolysiloxane, dimethylcyclopolysiloxane, methylphenylpolysiloxane, methylhydrogenpolysiloxane, higher alcohol-modified organopolysiloxane, and bisphenylpropyldimethicone; and fluoro oils such as fluoropolyethers and perfluoroalkyl ether silicones.

Examples of the semi-solid oils include cholesterol esters such as cholesteryl isostearate, cholesteryl hydroxystearate, and cholesteryl macadamiate; phytosterol esters such as phytosteryl/isostearyl/cetyl/stearyl/behenyl dimer dilinoleate, phytosteryl sunflowerseedate or phytosteryl oleate, bis-behenyl/isostearyl/phytosteryl dimer dilinoleyl dimer dilinoleate, phytosteryl macadamiate, phytosteryl/decyltetradecyl myristoyl methyl beta-alaninate, phytosteryl isostearate, phytosteryl oleate, and phytosteryl stearate; dipentaerythritol fatty acid esters such as dipentaerythritol hexaoxystearate and dipentaerythritol rosinate; triglycerides such as caprylic/capric triglyceride and caprylic/capric/myristic/stearic triglyceride; partially hydrogenated triglycerides such as hardened oils; animal oils and/or fats such as purified lanolin, lanosterol, and hydrogenated lanolin; higher fatty acids such as stearic acid, behenic acid, palmitic acid, and myristic acid; and petroleum jelly.

In addition, the cosmetic or stick-form cosmetic of the present invention can also be blended with ingredients which can usually be used in cosmetics, such as nonionic emulsifiers and various additives, as long as the effects of the present invention are not impaired.

Among the nonionic emulsifiers, nonionic emulsifiers having an HLB of 2 to 16 are usually preferable from the viewpoint of compatibility with oil. Particularly preferable among these are dipentaerythrityl tetrahydroxystearate/tetraisostearate (HLB 2), dipentaerythrityl hexahydroxystearate/stearate/rosinate (HLB 2), polyglyceryl-2 tetraisostearate (HLB 2), pentaerythrityl tetraisostearate (HLB 2), dipentaerythrityl tetraisostearate (HLB 3), polyglyceryl-2 triisostearate (HLB 3), polyglyceryl-3 beeswax (HLB 3), polyglyceryl-3 diisostearate (HLB 5), polyglyceryl-2 oleate (HLB 6), polyglyceryl-6 distearate (HLB 9), polyglyceryl-3 beeswax (HLB 10), and polyglyceryl-10 dioleate (HLB 12).

Examples of the various additives include amino acids such as glycine, alanine, serine, threonine, arginine, glutamic acid, aspartic acid, isoleucine, leucine, and valine; pyrrolidone carboxylic acid and sodium or zinc salts thereof, polyamino acids including polyglutamic acid and polyaspartic acid, and salts thereof, arabic gums, alginates, xanthan gum, hyaluronic acid, hyaluronates, chitin, chitosan, water-soluble chitin, carboxyvinyl polymer, carboxymethylcellulose, hydroxyethyl cellulose, hydroxypropyl trimethylammonium chloride, polydimethylmethylenepiperidium chloride, polyvinylpyrrolidone derivatives, quaternary ammonium cationized protein, collagen degradation product and derivatives thereof, and water-soluble polymers such as acylated proteins; sugar alcohols such as mannitol and alkylene oxide adducts thereof; and animal and plant extracts, nucleic acids, vitamins, enzymes, anti-inflammatory agents, bactericides, preservatives, antioxidants, ultraviolet absorbers, antiperspirants, pigments, colorants, oxidation dyes, pH adjusters, pearlescent agents, wetting agents, and polyhydric alcohols such as 1,3-butylene glycol.

The stick-form cosmetic can be produced, for example, as follows.

The base ingredients such as the oil composition of the present invention, an oil gelling agent, an antioxidant, and a preservative are heated and melted, and are uniformly mixed. A coloring agent is added thereto, and a kneading machine such as a roll mill is used to knead and uniformly disperse the mixture. Subsequently, the mixture is re-melted, added with a fragrance, defoamed and then poured into a mold, and rapidly cooled for solidification. The solidified product is removed from the mold, filled in a container, and subjected to a framing treatment as necessary.

Other features of the invention will become apparent in the course of the following descriptions of exemplary embodiments which are given for illustration of the invention and are not intended to be limiting thereof.

EXAMPLES

Production Example 1: Lauroyl Glutamic Acid Diester Mixture Having Melting Point of 35° C.

Into a reaction vessel equipped with a stirrer, a thermometer, and a gas inlet tube, 1 mole of N-lauroyl-L-glutamic acid and 2 moles of an alcohol mixture (phytosteryl alcohol, 2-octyldodecyl alcohol, and behenyl alcohol) were charged, and 600 ml of toluene was added thereto. Then, the mixture was heated and stirred, and added with 1 ml of sulfuric acid, and the reaction was allowed to take place while continuing the heating and stirring at 125° C. for about 8 hours in a nitrogen stream. During this time, by-product water was sufficiently removed. After the completion of the reaction, the mixture was neutralized with an aqueous solution of potassium hydroxide, and toluene was distilled off to obtain the target ester mixture. A portion of the obtained ester mixture was stirred and heated in potassium hydroxide/ethanol TS for 1 hour to completely hydrolyze the ester mixture. The content of various alcohols was examined, and their ratios were determined. The mass ratio of phytosteryl alcohol (cyclic alcohol, P), 2-octyldodecyl alcohol (branched alcohol, OD), and behenyl alcohol (linear alcohol, B) was B:OD:P=39:31:30, and the melting point of the obtained lauroyl glutamic acid diester mixture was 35° C.

Production Example 2: Lauroyl Glutamic Acid Diester Mixture Having Melting Point of 26.3° C.

Into a reaction vessel equipped with a stirrer, a thermometer, and a gas inlet tube, 1 mole of N-lauroyl-L-glutamic acid and 2 moles of an alcohol mixture (phytosteryl alcohol, 2-octyldodecyl alcohol, and behenyl alcohol) were charged, and 600 ml of toluene was added thereto. Then, the mixture was heated and stirred, and added with 5 g of para-toluenesulfonic acid monohydrate, and the reaction was allowed to take place while continuing the heating and stirring at 125° C. for about 8 hours in a nitrogen stream. During this time, by-product water was sufficiently removed. After the completion of the reaction, the mixture was neutralized with an aqueous solution of potassium hydroxide, and toluene was distilled off to obtain the target ester mixture. A portion of the obtained ester mixture was stirred and heated in potassium hydroxide/ethanol TS for 1 hour to completely hydrolyze the ester mixture. The content of various alcohols was examined, and their ratios were determined. The mass ratio of phytosteryl alcohol (cyclic alcohol, P), 2-octyldodecyl alcohol (branched alcohol, OD), and behenyl alcohol (linear alcohol, B) was B:OD:P=19.4:51.6:29, and the melting point of the obtained lauroyl glutamic acid diester mixture was 26.3° C.

Production Example 3: Lauroyl Glutamic Acid Diester Mixture Having Melting Point Lower than −24° C.

Into a reaction vessel equipped with a stirrer, a thermometer, and a gas inlet tube, 1 mole of N-lauroyl-L-glutamic acid and 2 moles of an alcohol mixture (phytosteryl alcohol and 2-octyldodecyl alcohol) were charged, and 600 ml of toluene was added thereto. Then, the mixture was heated and stirred, and added with 5 g of para-toluenesulfonic acid monohydrate, and the reaction was allowed to take place while continuing the heating and stirring at 125° C. for about 8 hours in a nitrogen stream. During this time, by-product water was sufficiently removed. After the completion of the reaction, the mixture was neutralized with an aqueous solution of potassium hydroxide, and toluene was distilled off to obtain the target ester mixture. A portion of the obtained ester mixture was stirred and heated in potassium hydroxide/ethanol TS for 1 hour to completely hydrolyze the ester mixture. The content of various alcohols was examined, and their ratios were determined. The mass ratio of phytosteryl alcohol (cyclic alcohol, P) and 2-octyldodecyl alcohol (branched alcohol, OD) was OD:P=75.5:24.5, and the melting point of the obtained lauroyl glutamic acid diester mixture was lower than −24° C.

Test Example 1: Comparison of Physical Properties of Oils

The lauroyl glutamic acid diester mixtures presented in Tables 1a and 1b were measured at the mass ratios as described therein, stirred at 60° C. for 10 minutes with a stirrer, and uniformly mixed. Each of the obtained oil mixtures was filled in a transparent glass container and cooled at 25° C. for 24 hours. The melting point, viscosity, transparency, elasticity, and gloss of each oil mixture were evaluated as follows. Tables 1a and 1b present the results.
Evaluation of Melting Point The melting point of each oil mixture was measured with a high-sensitivity differential scanning calorimeter (DSC-6200, manufactured by Hitachi High-Tech Science Corporation). Each of the oil mixtures presented in Table 1a was weighed at 10 mg into a predetermined cell, and the temperature was lowered from 60° C. to −20° C. at a rate of 2° C./min to measure the calorific value. The temperature at which the amount of heat released for each oil mixture was at the maximum was determined as the melting point of that oil mixture. Based on the following criteria, the appropriateness of the melting point was evaluated. Note that, for the oil composition of Example 1-1-4, the temperature was raised from −20° C. to 60° C. at a rate of 2° C./min to measure the calorific value, and the temperature at which the amount of heat absorbed was at the maximum was defined as the melting point.

Melting point is higher than 20° C. and 33° C. or lower: very preferable (A)

Melting point is higher than −20° C. and 20° C. or lower: preferable (B)

Melting point is higher than 33° C. or −20° C. or lower: not preferable (C)
Measurement of Complex Viscosity at 33° C.

The complex viscosity of each of the oil mixtures was evaluated with an instrument, AR-G2 (manufactured by TA Instruments). The temperature of the stand of the instrument was set to 33° C., and 0.5 g of the oil mixture was placed on the stand to give a 0.01 to 100% strain at a frequency of 1 Hz. At this time, the loss elastic modulus (G") and storage elastic modulus (G') values of the oil mixture were continuously measured. The maximum percent strain not causing a rapid change in G" and G' values was determined, and measurement was carried out by applying a vibration stress having an angular frequency of 0.1 to 100 rad/s to the oil mixtures at the percent strain. After the measurement, analysis was carried out by a conventional procedure to determine the complex viscosity of each oil mixture.
Evaluation of Transparency at 33° C.

Each of the oil mixtures presented in Table 1a was stored in a thermostatic chamber at 50° C. for 12 hours, and then allowed to stand in the thermostatic chamber at 33° C. for 24 hours. Immediately after each oil mixture was taken out of the thermostatic chamber, the transparency of the sample was visually checked and evaluated on a 9-point scale. The oil mixture with the highest transparency was scored as 5 points, and the oil mixture with the lowest transparency was scored as 1 point. Based on these scores, the transparency was evaluated based on the following criteria.

Transparency score is 2.0 or more: very preferable (A)

Transparency score is 1.5 or more and less than 2.0: preferable (B)

Transparency score is less than 1.5: not preferable (C)
Evaluation of Elasticity The viscoelasticity of each of the oil mixtures was evaluated with an instrument, AR-G2 (manufactured by TA Instruments). On the stand of the instrument, 0.5 g of the oil mixture was placed, and a strain of 0.001 to 100 was applied to the oil mixture at 35° C. At this time, the loss elastic modulus (G") and storage elastic modulus (G') values of the oil mixture were continuously measured, and the ratio (tan $\delta$=G"/G') was determined. Based on the value of tan $\delta$ when the strain was 1, it was evaluated whether or not the oil mixture had sufficient elasticity required for makeup duration. Note that FIG. 1 illustrates the viscoelastic profiles of the oil mixtures of Comparative Example 1-1-1, Example 1-1-4, and Example 1-1-13.

tan $\delta$ is 10 or less: very preferable (A)

tan $\delta$ is more than 10 and 100 or less: preferable (B)

tan $\delta$ is more than 100: not preferable (C)
Evaluation of Oil Gloss

The gloss of each oil mixture was evaluated by measuring the oil gloss index with a gloss index measuring instrument (Gloss Checkers IG-331, manufactured by HORIBA, Ltd.).

After 30 mg of each oil mixture was applied on a black bioskin plate (manufactured by Beaulax) in a circular shape having a diameter of 3 cm, the bioskin was warmed on a hot plate for 10 minutes so that the surface temperature of the bioskin was 33° C. After 10 minutes, the gloss index measuring instrument was used to measure the gloss index of the oil. Based on the obtained gloss index value, oil gloss was evaluated according to the following criteria.

Gloss index is 75 or more: very high gloss, very preferable (A)

Gloss index is 65 or more and less than 75: high gloss, preferable (B)

Gloss index is 50 or more and less than 65: not very high gloss, not very preferable (C)

Gloss index is less than 50: low gloss, definitely not preferable (D)

TABLE 1a

Comparison of Physical Properties of Oils Required for Excellent Stability and Texture Properties of Lipstick

| | Lauroyl Glutamic Acid Diester Mixture Having Melting Point of −20° C. or Lower (Mass Ratio) | Lauroyl Glutamic Acid Diester Mixture Having Melting Point of 20 to 32° C. (Mass Ratio) | Lauroyl Glutamic Acid Diester Mixture Having Melting Point Higher Than 33° C. (Mass Ratio) | Complex Viscosity at 33° C. Pa · s | Transparency at 33° C. | Melting Point ° C. | Qualitative Evaluation of Transparency at 33° C. | Qualitative Evaluation of Melting Point | Qualitative Evaluation of Elasticity Required for Makeup Duration |
|---|---|---|---|---|---|---|---|---|---|
| Comparative Example 1-1-1 | 100 | | | 0.9 | 5 | <−20 | A | C | C |
| Comparative Example 1-1-2 | | | 100 | 45000 | 1 | 35 | C | C | A |
| Example 1-1-1 | 80 | | 20 | 5.5 | 4 | 14 | A | B | A |
| Example 1-1-2 | 50 | | 50 | 120 | 2 | 29 | A | A | A |
| Example 1-1-3 | 20 | | 80 | 3000 | 2 | 32 | A | A | A |
| Example 1-1-4 | 80 | 20 | | 4.9 | 4.5 | −10 | A | B | A |
| Example 1-1-5 | 50 | 50 | | 6.5 | 4.5 | −5 | A | B | A |
| Example 1-1-6 | 20 | 80 | | 7.5 | 3.5 | 23 | A | A | A |
| Example 1-1-7 | | 80 | 20 | 18 | 2 | 28 | A | A | A |
| Example 1-1-8 | | 50 | 50 | 710 | 2 | 31 | A | A | A |
| Example 1-1-9 | | 20 | 80 | 14000 | 1.5 | 33 | B | A | A |
| Example 1-1-10 | 60 | 20 | 20 | 3.6 | 3 | 28 | A | A | A |
| Example 1-1-11 | 60 | 40 | | 5.9 | 4 | 13 | A | B | A |
| Example 1-1-12 | 60 | | 40 | 21 | 3 | 27 | A | A | A |
| Example 1-1-13 | 33 | 34 | 33 | 38 | 3 | 27 | A | A | B |

TABLE 1b

Comparison of Oil Gloss Required for Excellent Texture Properties of Lipstick

| | Lauroyl Glutamic Acid Diester Mixture Having Melting Point of −20° C. or Lower (Mass Ratio) | Lauroyl Glutamic Acid Diester Mixture Having Melting Point of 20 to 32° C. (Mass Ratio) | Lauroyl Glutamic Acid Diester Mixture Having Melting Point Higher Than 33° C. (Mass Ratio) | Gloss Index of Oil at 33° C. | Qualitative Evaluation of Gloss at 33° C. |
|---|---|---|---|---|---|
| Comparative Example 1-2-1 | 100 | | | 72 | B |
| Comparative Example 1-2-2 | | 100 | | 61 | C |
| Comparative Example 1-2-3 | | | 100 | 31 | D |
| Example 1-2-1 | 50 | 50 | | 75 | A |
| Example 1-2-2 | 60 | 20 | 20 | 72 | B |
| Example 1-2-3 | 60 | 40 | | 76 | A |
| Example 1-2-4 | | 80 | 20 | 70 | B |
| Example 1-2-5 | 50 | | 50 | 68 | B |

Test Example 2: Evaluation of Balance Between Texture Properties and Stability of Lipstick Preparation of Lipstick Ceresin wax (manufactured by Nikko Rica Corporation) at 15 percent by mass, isotridecyl isononanoate (manufactured by The Nisshin Oillio Group, Ltd.) at 40 percent by mass as a low-viscosity oil, and an oil mixture described in Table 2 at 45 percent by mass were weighed, stirred for 20 minutes with a stirrer while being heated at 90° C., and mixed uniformly. The obtained mixture was filled in a plastic lipstick container having a diameter of 10 mm and cooled at 25° C. for 24 hours to obtain each lipstick. For the obtained lipsticks, the balance between texture properties and stability was evaluated as follows. Table 2 presents the results.

Measurement of Breaking Strength of Lipstick

The breaking strength of the lipstick was evaluated with a FUDOH Rheometer (manufactured by RHEOTECH). The lipstick was pulled out by 15 mm, then fixed, and measured at 25° C. with a jig of a toothed pushrod. The maximum load value when the jig reached a depth of 10 mm at a rate of 6 cm/min was defined as the breaking strength.

Measurement of Coefficient of Dynamic Friction of Stick

The slipperiness of the lipstick was evaluated with Tribomaster (manufactured by Trinity-Lab). After the lipstick was pulled out by 3 mm, the sample was fixed to the upper part of the instrument, and slid over artificial leather at a rate of 2 mm/s to carry out measurement. The average value of the coefficient of dynamic friction for two reciprocations over a distance of 50 cm was measured.

Evaluation of Balance between Texture Properties and Stability of Lipstick

It is said that the higher the breaking strength of the lipstick, the more the lipstick is resistant to breakage and the better the stability. On the other hand, it can be judged that, as the coefficient of dynamic friction of the lipstick decreases, the lipstick has better slipperiness and smoother feel. In other words, it can be judged that the larger the value obtained by dividing the breaking strength value of each lipstick by the coefficient of dynamic friction of that lipstick, the better the stability and the texture properties of the lipstick. Based on the value of lipstick breaking strength value/lipstick dynamic friction coefficient, the balance between the texture properties and stability of the lipstick was evaluated as follows.

The value of lipstick breaking strength value/lipstick dynamic friction coefficient is 1550 or more: very good balance (A)

less than 1550 and 1500 or more: not very good balance (B)

less than 1500: poor balance (C).

TABLE 2

Evaluation of Balance between Texture Properties and Stability of Lipstick

| | Lauroyl Glutamic Acid Diester Mixture Having Melting Point of −20° C. or Lower (Mass Ratio) | Lauroyl Glutamic Acid Diester Mixture Having Melting Point of 20 to 32° C. (Mass Ratio) | Lauroyl Glutamic Acid Diester Mixture Having Melting Point Higher Than 33° C. (Mass Ratio) | Balance between Texture Properties and Stability of Lipstick (Stick Breaking Strength Value/Stick Dynamic Friction Coefficient Value) | Qualitative Evaluation of Stick Breaking Strength/Stick Dynamic Friction Coefficient |
|---|---|---|---|---|---|
| Comparative Example 2-1 | 100 | | | 1388.176 | C |
| Comparative Example 2-2 | | 100 | | 1490.619 | C |
| Example 2-1 | 80 | 20 | | 1602.83 | A |
| Example 2-2 | 20 | 80 | | 1720.553 | A |
| Example 2-3 | | 20 | 80 | 1811.592 | A |
| Example 2-4 | | 80 | 20 | 1565.749 | A |

Test Example 3: Evaluation of Temporal Stability of Breaking Strength of Lipstick Preparation of Lipstick Ceresin wax (manufactured by Nikko Rica Corporation) at 15 percent by mass, isotridecyl isononanoate (manufactured by The Nisshin Oillio Group, Ltd.) at 40 percent by mass as a low-viscosity oil, and an oil mixture described in Table 3 at 45 percent by mass were weighed, stirred for 20 minutes with a stirrer while being heated at 90° C., and mixed uniformly. The obtained mixture was filled in a plastic lipstick container having a diameter of 10 mm and cooled at 25° C. for 24 hours to obtain each lipstick. For the obtained lipsticks, the temporal stability was evaluated as follows. Table 3 presents the results.

Evaluation of Temporal Stability

For the obtained lipsticks, the breaking strength was measured in the same manner as in Test Example 2 (initial breaking strength value). Subsequently, each of the lipsticks was stored in a thermostatic chamber at 50° C. for 1 week, taken out of the thermostatic chamber, and allowed to stand at 25° C. for 24 hours. The breaking strength of the lipstick after standing was measured (breaking strength value after storage at high temperature). The rate of temporal decrease in the lipstick breaking strength was determined from the following equation Rate of decrease in breaking strength=100×(initial breaking strength value−breaking strength value after storage at high temperature)/initial breaking strength value.

According to the following evaluation criteria, the temporal stability of the lipstick was evaluated from the rate of decrease in the breaking strength.

Rate of decrease in breaking strength is 10% or less: very good temporal stability (A)

Rate of decrease in breaking strength is more than 10% and less than 14%: not very good temporal stability (B)

Rate of decrease in breaking strength is 14% or more: poor temporal stability (C)

TABLE 3

Evaluation of Temporal Stability of Lipstick

| | Lauroyl Glutamic Acid Diester Mixture Having Melting Point of −20° C. or Lower (Mass Ratio) | Lauroyl Glutamic Acid Diester Mixture Having Melting Point of 20 to 32° C. (Mass Ratio) | Lauroyl Glutamic Acid Diester Mixture Having Melting Point Higher Than 33° C. (Mass Ratio) | Rate of Temporal Decrease in Lipstick Breaking Strength (%) | Qualitative Evaluation of Improvement in Temporal Stability |
|---|---|---|---|---|---|
| Comparative Example 3-1 | 100 | | | 14 | C |
| Comparative Example 3-2 | | 100 | | 27 | C |
| Comparative Example 3-3 | | | 100 | 20 | C |
| Example 3-1 | 50 | 50 | | 2 | A |
| Example 3-2 | 50 | | 50 | −11 | A |
| Example 3-3 | 80 | 20 | | 10 | A |
| Example 3-4 | 80 | | 20 | 8 | A |

Test Example 4: Sensory Evaluation of Oil Mixture (Evaluation of Feel)

Four expert panelists evaluated the spreadability and the non-stickiness of each oil mixture according to the following criteria.

| Close Adhesion to Skin | |
|---|---|
| 1) Close adhesion is very good | 4 points |
| 2) Close adhesion is good | 3 points |
| 3) Close adhesion is not very good | 2 points |
| 4) Close adhesion is definitely not good | 1 point |
| Slippery Feel | |
| 1) Slippery feel is very good | 4 points |
| 2) Slippery feel is good | 3 points |
| 3) Slippery feel is not very good | 2 points |
| 4) Slippery feel is definitely not good | 1 point |
| Non-Stickiness | |
| 1) Definitely not sticky | 4 points |
| 2) Not sticky | 3 points |
| 3) Slightly sticky | 2 points |
| 4) Very sticky | 1 point |

The following judgments were made based on the average score of the evaluations of the four expert panelists. Table 4 presents the results.

Average evaluation point is 3.5 or more: very preferable (A)

Average evaluation point is 2.5 or more and less than 3.5: rather preferable (B)

Average evaluation point is 1.5 or more and less than 2.5: not very preferable (C)

Average evaluation point is less than 1.5: definitely not preferable (D)

TABLE 4

Sensory Evaluation of Oil

| | Close Adhesion to Skin | Slippery Feel | Non-Stickiness |
|---|---|---|---|
| Oil Mixture of Comparative Example 1-1-1 | C | A | A |
| Oil Mixture of Comparative Example 1-1-2 | B | B | A |
| Oil Mixture of Comparative Example 1-1-3 | A | C | A |
| Oil Mixture of Example 1-1-3 | A | A | A |
| Oil Mixture of Example 1-1-5 | A | A | A |
| Oil Mixture of Example 1-1-2 | A | A | A |
| Oil Mixture of Example 1-1-7 | A | A | A |

Test Example 5: Evaluation of Feel by Lipstick Formula

Preparation of Lipstick

The ingredients presented in Tables 5a and 5b were stirred for 20 minutes with a stirrer while being heated at 90° C., and were uniformly mixed. The obtained mixture was uniformly mixed and dispersed with a roll mill. The dispersion product was further heated at 90° C. into the liquid state, then filled in a plastic lipstick container having a diameter of 10 mm, and cooled at 25° C. for 24 hours to obtain each lipstick.

Sensory Evaluation of Lipstick Formulation

Four expert panelists evaluated the spreadability and the non-stickiness of Example 4 according to the following criteria.

| Melting Smooth Feel | |
|---|---|
| 1) Very good smooth feel | 4 points |
| 2) Good smooth feel | 3 points |
| 3) Not very good smooth feel | 2 points |
| 4) Definitely not smooth feel | 1 point |
| Uniform Spread over Lip Surface | |
| 1) Very good spread uniformity | 4 points |
| 2) Good spread uniformity | 3 points |
| 3) Not very good spread uniformity | 2 points |
| 4) Definitely not good spread uniformity | 1 point |
| Transparent Gloss | |
| 1) Very good transparent gloss | 4 point |
| 2) Good transparent gloss | 3 points |
| 3) Not very good transparent gloss | 2 points |
| 4) Definitely not good transparent gloss | 1 point |

-continued

| Makeup Duration/Persistence | |
|---|---|
| 1) Very good makeup duration/persistence | 4 points |
| 2) Good makeup duration/persistence | 3 points |
| 3) Not very good makeup duration/persistence | 2 points |
| 4) Definitely not good makeup duration/persistence | 1 point |

The following judgments were made based on the average score of the evaluations of the four expert panelists. Tables 5a and 5b present the results.

Average evaluation point is 3.5 or more: very preferable (A)

Average evaluation point is 2.5 or more and less than 3.5: rather preferable (B)

Average evaluation point is 1.5 or more and less than 2.5: not very preferable (C)

Average evaluation point is less than 1.5: definitely not preferable (D)

TABLE 5a

Sensory Evaluation of Lipstick

| Physical Property and Characteristic | Ingredient Name | Formulation 1 (Mass Ratio) | Formulation 2 (Mass Ratio) | Formulation 3 (Mass Ratio) | Formulation 4 (Mass Ratio) |
|---|---|---|---|---|---|
| High Viscosity and Low Polarity Oil | Hydrogenated Polyisobutene | 10 | 10 | 10 | 10 |
| Low Viscosity and High Polarity Oil | Caprylic/Capric Triglyceride | 10 | 10 | 10 | 10 |
| Low Viscosity and High Polarity Oil | Octyldodecanol | 10 | 10 | 10 | 10 |
| Low Viscosity and Low Polarity Oil | Squalane | 10 | 10 | 10 | 10 |
| High Viscosity and High Polarity Oil | Polyglyceryl-2 Triisostearate | 10 | 10 | 10 | 10 |
| High Viscosity and High Polarity Oil | Diisostearyl Malate | 10 | 10 | 10 | 10 |
| | Oil Mixture of Comparative Example 1-1-1 | 21 | | | |
| | Oil Mixture of Comparative Example 1-1-2 | | 21 | | |
| | Oil Mixture of Example 1-1-7 | | | 21 | |
| | Oil Mixture of Example 1-1-10 | | | | 21 |
| Wax Having Melting Point of 70° C. or Higher and Lower than 77° C. | Ceresin Wax | 9 | 9 | 9 | 9 |
| Wax Having Melting Point of 65° C. or Lower | Purified Paraffin Wax | 2 | 2 | 2 | 2 |
| Branched Wax | Microcrystalline Wax | 3 | 3 | 3 | 3 |
| Oil-Soluble Colorant | Red No. 202 (C.I. 15850) | 2 | 2 | 2 | 2 |
| Inorganic Pigment | Titanium Oxide | 1 | 1 | 1 | 1 |
| Inorganic Pigment | Iron Oxide, Red | 0.1 | 0.1 | 0.1 | 0.1 |
| Inorganic Pigment | Iron Oxide, Yellow | 0.2 | 0.2 | 0.2 | 0.2 |
| Inorganic Pigment | Iron Oxide, Black | 0.05 | 0.05 | 0.05 | 0.05 |
| Inorganic Pigment | Zinc Oxide | 0.1 | 0.1 | 0.1 | 0.1 |
| Lake Colorant | Blue No. 1 (C.I. 42090) | 0.25 | 0.25 | 0.25 | 0.25 |
| Lake Colorant | Yellow No. 4 (C.I. 19140) | 0.2 | 0.2 | 0.2 | 0.2 |
| Lake Colorant | Yellow No. 5 (C.I. 15985) | 0.1 | 0.1 | 0.1 | 0.1 |
| Lake Colorant | Red No. 104 (C.I. 45410) | 1 | 1 | 1 | 1 |
| | Total (Mass Ratio) | 100 | 100 | 100 | 100 |
| | Melting Smooth Feel | B | C | A | A |
| | Uniform Spread over Lip Surface | A | C | A | A |

TABLE 5a-continued

Sensory Evaluation of Lipstick

| Physical Property and Characteristic | Ingredient Name | Formulation 1 (Mass Ratio) | Formulation 2 (Mass Ratio) | Formulation 3 (Mass Ratio) | Formulation 4 (Mass Ratio) |
|---|---|---|---|---|---|
| | Transparent Gloss | A | C | A | A |
| | Makeup Duration/Persistence | C | A | A | A |

TABLE 5b

Sensory Evaluation of Lipstick

| Physical Property and Characteristic | Ingredient Name | Formulation 3 (mass ratio) | Formulation 4 (mass ratio) |
|---|---|---|---|
| High Viscosity and Low Polarity Oil | Hydrogenated Polyisobutene | 19 | 25 |
| Low Viscosity and High Polarity Oil | Caprylic/Capric Triglyceride | 10 | 10 |
| Low Viscosity and High Polarity Oil | Octyldodecanol | 10 | 10 |
| Low Viscosity and Low Polarity Oil | Squalane | 10 | 10 |
| High Viscosity and High Polarity Oil | Polyglyceryl-2 Triisostearate | 10 | 10 |
| High Viscosity and High Polarity Oil | Diisostearyl Malate | 10 | 10 |
| Moisturizer | 1,3-butylene glycol | 3 | 3 |
| | Water | 2 | 2 |
| | Oil Mixture of Example 1-1-13 | 10 | 5 |
| Wax Having Melting Point of 85° C. or Higher | Polyethylene Wax | | 7 |
| Wax Having Melting Point of 77° C. or Higher and Lower than 85° C. | Linear Synthetic Hydrocarbon Wax Having Molecular Weight of 300 to 1000 | 8 | |
| Wax Having Melting Point of 65° C. or Lower | Purified Paraffin Wax | 2 | 2 |
| Lake Colorant | Red No. 104 (C.I. 45410) | 1 | 1 |
| Water-Soluble Colorant | Red No. 201 (C.I. 15850) | 1 | 1 |
| Inorganic Pigment | Titanium Oxide | 1 | 1 |
| Inorganic Pigment | Iron Oxide, Red | 0.5 | 0.5 |
| Inorganic Pigment | Iron Oxide, Yellow | 0.3 | 0.3 |
| Inorganic Pigment | Iron Oxide, Black | 0.05 | 0.05 |
| Inorganic Pigment | Zinc Oxide | 1 | 1 |
| Lake Colorant | Blue No. 1 (C.I. 42090) | 0.25 | 0.25 |
| Lake Colorant | Yellow No. 4 (C.I. 19140) | 0.5 | 0.5 |
| Lake Colorant | Yellow No. 5 (C.I. 15985) | 0.4 | 0.4 |
| | Total (Mass Ratio) | 100 | 100 |
| | Melting Smooth Feel | A | A |
| | Uniform Spread over Lip Surface | A | A |
| | Transparent Gloss | A | A |
| | Makeup Duration/Persistence | A | A |

Formulation Example 1: Lip Care Stick

The ingredients presented in Table 6 were stirred for 20 minutes with a stirrer while being heated at 90° C., and were uniformly mixed. The obtained mixture was uniformly mixed and dispersed with a roll mill. The dispersion product was further heated at 90° C. into the liquid state, then filled in a plastic lipstick container having a diameter of 10 mm, and cooled at 25° C. for 24 hours to obtain a lip care stick. The obtained lip care stick was glossy, had an improved stability, and had a smooth feel.

TABLE 6

Formulation Example 1

| Ingredient Name | (Mass Ratio) |
| --- | --- |
| Hydrogenated Polyisobutene | 25 |
| Diisostearyl Malate | 15 |
| Dipentaerythrityl Hexahydroxystearate/Hexastearate/Hexarosinate | 10 |
| Neopentyl Glycol Dicaprate | 7 |
| Diphenylsiloxy Phenyl Trimethicone | 5 |
| Triethylhexanoin | 5 |
| Pentaerythrityl Tetraisostearate | 3 |
| Dipentaerythrityl Pentaisostearate | 3 |
| Polyethylene Wax | 10 |
| Bis-Behenyl/Isostearyl/Phytosteryl Dimer Dilinoleyl Dimer Dilinoleate | 3 |
| Phytosteryl/Isostearyl/Cetyl/Stearyl/Behenyl Dimer Dilinoleate | 3 |
| Oil Mixture of Example 1-1-1 | 2 |
| Squalane | 3 |
| Polyglyceryl-2 Triisostearate | 3 |
| Water | 3 |
| Total (Mass Ratio) | 100 |

Formulation Example 2: Red Lipstick

The ingredients presented in Table 7 were stirred for 20 minutes with a stirrer while being heated at 90° C., and were uniformly mixed. The obtained mixture was uniformly mixed and dispersed with a roll mill. The dispersion product was further heated at 90° C. into the liquid state, then filled in a plastic lipstick container having a diameter of 10 mm, and cooled at 25° C. for 24 hours to obtain a red lipstick. The obtained red lipstick was glossy, had a high color development, and had a melting feel.

TABLE 7

Formulation Example 2

| Ingredient Name | (Mass Ratio) |
| --- | --- |
| Hydrogenated Polyisobutene | 20 |
| Diisostearyl Malate | 15 |
| Bis-Diglyceryl Polyacyladipate-2 | 10 |
| Dipentaerythrityl Tetraisostearate | 5 |
| Diphenylsiloxy Phenyl Trimethicone | 5 |
| Polyethylene Wax | 10 |
| Bis-Behenyl/Isostearyl/Phytosteryl Dimer Dilinoleyl Dimer Dilinoleate | 3 |
| Phytosteryl Macadamiate | 2 |
| Oil Mixture of Example 1-1-4 | 15 |
| Titanium Oxide | 3 |
| Squalane | 2 |
| Polyglyceryl-3 Diisostearate | 6 |
| Honey | 1 |
| Red No. 202 (C.I. 15850) | 3 |
| Total (Mass Ratio) | 100 |

Formulation Example 3: Red Liquid Lipstick

The ingredients presented in Table 8 were stirred for 20 minutes with a stirrer while being heated at 90° C., and were uniformly mixed. The obtained mixture was uniformly mixed and dispersed with a roll mill to obtain a red liquid lipstick. The obtained red liquid lipstick was glossy, good in adhesion, and excellent in makeup duration and stability.

TABLE 8

Formulation Example 3

| Ingredient Name | (Mass Ratio) |
| --- | --- |
| Liquid Lanolin | 20 |
| Diisostearyl Malate | 10 |
| Jojoba Oil | 5 |
| Liquid Paraffin | 5 |
| Dimethicone | 5 |
| Polyglycerol Polyether Modified Silicone ("SOFCARE GS-G manufactured by Kao Corporation") | 5 |
| Pearlescent Agent (such as mica and polyethylene) | 5 |
| Dextrin Palmitate | |
| Bis-Behenyl/Isostearyl/Phytosteryl Dimer Dilinoleyl Dimer Dilinoleate | 10 |
| Phytosteryl Macadamiate | 2 |
| Oil Mixture of Example 1-1-9 | 12 |
| Titanium Oxide | 3 |
| Iron Oxide | 1 |
| Squalane | 3 |
| Polyglyceryl-6 Distearate | 3 |
| Glycerin | 3 |
| Red No. 201 | 3 |
| Water | 5 |
| Total (Mass Ratio) | 100 |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An oil composition, comprising two or more mixtures selected from the group consisting of a lauroyl glutamic acid diester mixture having a melting point higher than 33° C., a lauroyl glutamic acid diester mixture having a melting point of 20 to 32° C., and a lauroyl glutamic acid diester mixture having a melting point of −20° C. or lower,
  wherein one of the two or more lauroyl glutamic acid diester mixtures is present in an amount higher than 10% by mass, and another one of the two or more lauroyl glutamic acid diester mixtures is present in an amount higher than 10% by mass and the oil composition does not comprise a cholesteryl ester,
  wherein the lauroyl glutamic acid diester mixture having a melting point higher than 33° C. is obtained by reacting N-lauroyl-L-glutamic acid with an alcohol mixture containing two or more alcohols and the alcohol mixture is an alcohol mixture of (a) 2-octyldodecyl alcohol or isostearyl alcohol, (b) phytosteryl alcohol, and (c) behenyl alcohol,
  wherein the lauroyl glutamic acid diester mixture having a melting point of 20 to 32° C. is obtained by reacting N-lauroyl-L-glutamic acid with an alcohol mixture containing two or more alcohols and the alcohol mixture is an alcohol mixture of (a) 2-octyldodecyl alcohol or isostearyl alcohol, (b) phytosteryl alcohol, and (c) behenyl alcohol,
  wherein the lauroyl glutamic acid diester mixture having a melting point of −20° C. or lower is obtained by reacting N-lauroyl-L-glutamic acid with an alcohol mixture containing two or more alcohols and the alcohol mixture is an alcohol mixture of (a) 2-octyldodecyl alcohol or isostearyl alcohol and (b) phytosteryl alcohol.

2. The oil composition according to claim 1, wherein a complex viscosity of the oil composition at 33° C. is 1 to 25000 Pa·s.

3. The oil composition according to claim 1, wherein a tan δ (=G"/G') of the oil mixture is 100 or less
  wherein G" is a loss elastic modulus and G' is storage elastic modulus.

4. A cosmetic, comprising an oil composition according to claim 1 and at least one ingredient selected from the group consisting of a pigment and a colorant.

5. The cosmetic according to claim 4, which is usable on a lip surface.

6. A stick-form cosmetic, comprising an oil composition according to claim 1, and an oil gelling agent having a melting point of 40° C. or higher.

7. The stick-form cosmetic according to claim 6, further comprising at least one ingredient selected from the group consisting of a pigment and a colorant.

8. The stick-form cosmetic according to claim 6, is usable on a lip surface.

* * * * *